United States Patent [19]

Blount

[11] 4,089,883

[45] May 16, 1978

[54] PROCESS FOR THE PRODUCTION OF ORGANIC HYDROXY SILICATE COMPOUNDS AND THEIR CONDENSATION PRODUCTS

[76] Inventor: David H. Blount, 5450 Lea St., San Diego, Calif. 92105

[21] Appl. No.: 765,050

[22] Filed: Feb. 2, 1977

Related U.S. Application Data

[63] Continuation-in-part of Ser. No. 703,925, Jul. 9, 1976, Pat. No. 4,011,253, and Ser. No. 589,626, Jun. 23, 1975, abandoned.

[51] Int. Cl.[2] .......................... C07F 7/18; C07F 7/04

[52] U.S. Cl. ...................... 260/448.8 R; 260/448.2 E; 536/1; 536/102

[58] Field of Search .................... 260/448.2 E, 209 R, 260/233.3 R, 448.8 R

[56] References Cited

U.S. PATENT DOCUMENTS 4,028,391 6/1977 Foley ........................ 260/448.2 E X

*Primary Examiner*—Paul F. Shaver

[57] ABSTRACT

A dry granular alkali metal metasilicate is chemically reacted with a concentrated acid or an acid hydrogen containing salt to produce white granular silicic acid compounds which will react chemically with a polyhydroxy alcohol by using an alkaline compound as a catalyst and by heating the mixture.

5 Claims, No Drawings

PROCESS FOR THE PRODUCTION OF ORGANIC HYDROXY SILICATE COMPOUNDS AND THEIR CONDENSATION PRODUCTS

CROSS-REFERENCE TO RELATED CO-PENDING APPLICATION

This application is a continuation-in-part of U.S. Pat. application Ser. No. 703,925, filed July 9, 1976 and U.S. Pat. No. 4,011,253 application Ser. No. 589,626, filed June 23, 1975, now abandoned.

BACKGROUND OF THE INVENTION

This invention relates to a process for the production of organic hydroxy silicate compounds and their condensation products.

The silicic acid compound used in this process may be produced by the chemical reaction of a dry alkali metal metasilicate with a mineral acid or an acid hydrogen containing salt. The silicic acid may also be produced by any commonly known methods.

The silicic acid used in the following examples was produced by reacting dry granular alkali metal metasilicate with a hydrogen containing acid salt or a concentrated mineral acid. The white granular silicic acid is washed with water, filtered and then air dried at 25° to 75° C. The white granular silicic acid was analyzed by Infrared Analysis, using the IR KBr disc method. The Infrared Analysis was very similar to that obtained with Mallinckrodt's hydrated silica except for the area which shows the presence of Si—H bonds. The Mallinckrodt's hydrated silica ($SiO_2.xH_2O$) has a molecular weight off $60.09.xH_2O$. The said silicic acid contains an active hydrogen which will reduce silver nitrate in an aqueous solution, which is evident that Si—H bonds are present.

When the said silicic acid is heated to much above 105° C, silicon dioxide with a molecular weight of about 60 is produced. On further heating, it has a melting point of 1650° C. In cryoscopic and ebullioscopic determination, the silicic acid produced was not soluble in any common organic solvent but was readily soluble in dilute alkali metal hydroxide aqueous solutions.

The molecular weight was determined from the boiling point elevation of said silicic acid in a 6N sodium hydroxide solution and indicated a molecular weight of $78 \pm 25$ gm/mol. This type of reactive solution normally changes the molecular species. However, this would seem to indicate the absence of a polymeric form of silicate. This analysis may indicate a possible formula of $HSi(OH)_3$ (orthosilicoformic acid) and $H_2SiO_3$ (metasilicic acid). The orthosilicoformic acid, when dried, will lose water to form silicoformic acid (H.SiO.OH).

The exact course of the reactions which take place during the process to produce organic hydroxy silicate compounds and condensation products cannot be determined with 100% certainty.

Organic hydroxy silicate compounds and poly (organic hydroxy silicate) polymers will chemically react with diisocyanates to produce useful and novel foams and resins which are soluble in organic solvents; these solutions may be used as a protective coating on wood. The novel organic hydroxy silicate compounds and polymers will react chemically with dicarboxylic acids and anhydrides by mixing and heating above the melting point of the dicarboxylic acid or anhydrides for 30 to 90 minutes while agitating to produce a poly (alkyd silicate) resin which is soluble in organic solvents such as acetic acid. When painted on wood, the solution produces a clear, tough, protective coating. The poly (alkyd silicate) resin may be molded into useful objects with heat and pressure. The hydroxy silicate compounds may be ground into a fine powder and used as a filler in paints, varnishes, impregnants, laminates and molding powders.

SUMMARY OF THE INVENTION

I have discovered that a silicic acid compound produced by the chemical reaction of a dry alkali metasilicate with a concentrated mineral acid or an acid hydrogen containing salt will react chemically with polyhydroxy alcohols and vegetable oils containing hydroxy radicals in the presence of a small amount of an alkali catalyst at a temperature below the boiling temperature of the polyhydroxy alcohol to produce an organic hydroxy silicate compound. On further heating of the organic hydroxy silicate compound, a poly (organic hydroxy silicate) polymer is produced.

Various alkaline metal and alkali metal metasilicates may be used in the process, but dry granular sodium metasilicate is preferred.

Various mineral acids and acid hydrogen containing salts may be used in this process, but concentrated sulfuric acid and sodium hydrogen sulfate are preferred.

Various alkali compounds such as alkali metal carbonates, hydroxides, oxides and alkali metal salts of weak acids may be used as the catalyst in the chemical reaction to produce organic hydroxy silicate compounds and condensation products. The most useful alkali metal carbonate is sodium carbonate, but other alkali metal carbonates such as potassium carbonate may be used. The most useful alkali metal hydroxide is sodium hydroxide, but potassium hydroxide and other alkali metal hydroxides may be used as the catalyst. Sodium silicate may also be used as the catalyst. Best results are obtained when the alkali catalyst is added in the amount of 1% to 10% of the weight of the reactants, silicic acid compound and organic polyhydroxyl alcohol.

The alkali catalyst is necessary in this process because when an organic polyhydroxyl alcohol is heated with a silicic acid compound without an alkali catalyst, no organic hydroxy silicate compound is produced. It is possible to produce a colloidal dispersion of silica hydrogel in polyols when a polyhydroxy alcohol is heated with silicic acid without the presence of an alkali catalyst but not an organic hydroxy silicate.

The term "polyhydroxy alcohols", as used in the Specification and Claims, comprises:

(a) Glycerol, glycerol monochlorohydrin, (b) Glycols with free OH radicals, such as ethylene glycol, propylene glycol, butylene glycol, trimethylene glycol, tetramethylene glycol, pentamethylene glycol, hexamethylene glycol, diethylene glycol, triethylene glycol, dipropylene glycol, tetraethylene glycol, polyethylene glycols and ether glycol such as sold under various trade names, e.g. Carbitol, Cellosole, Pluronics, Carbowax and Ucon.

(c) Bisphenol A, resorcinol, bis (B-hydroxyethyl) terephthlate, pentaerythritol, trimethol propane, trimethol ethane, 2,2-oxyethanol.

(d) Carbohydrates, such as glucose, mannose, fructose, molasses, cane sugar, dextrines, starches, corn syrup and maple syrup.

(e) Vegetable oils, such as castor oil.

(f) Any mixture of the above polyhydroxy alcohols.

Infrared KBr disc analysis was ran on the products. The Infrared KBr disc anaylsis was ran on the poly (glycerol silicate) polymer and then was compared to a glycerol Infrared Analysis standard. The Infrared KBr disc analysis of the poly (glycerol silicate) polymer, as produced by this instant specification, shows that some of the identifiable absorption peaks, as found in the glycerol standard, are appreciably changed. The wave numbers at 1400, 1200 and 980 $cm^{-1}$ appear to be minimized or lost; those at 1450, 740 and $615^{-1}$ wave numbers have split into a triplet. These changes indicate that the silicic acid reacted with the glycerol to produce poly (glycerol silicate) polymer. The poly (glycerol silicate) polymer forms a clear, brown solution in polyhydroxy alcohols and acetic acid. The brown poly (glycerol silicate) polymer does not gel as does silicic acid suspension in polyhydroxy alcohols. The poly (glycerol silicate) polymer has a softening point of about 35° C and a melting point of about 70° C. The other organic polyhydroxy silicates and polymers produced by this instant specification show changes on KBr disc analysis which indicates that the silicic acid reacts chemically with the polyhydroxy alcohols to produce organic polyhydroxy silicates and polymers.

The primary object of the present invention is to produce organic polyhydroxy silicates and polymers. Another object is to produce organic polyhydroxy silicates and polymers which will react chemically with diisocyanates to produce useful foams and resins. Still another object is to produce organic polyhydroxy silicates and polymers which will react chemically with dicarboxylacids and anhydrides to produce useful resins. A further object is to produce polyhydroxy silicate compounds to be used in paints and varnishes as a filler. Another object is to produce organic polyhydroxy silicate compounds and polymers that are soluble in organic solvents and which may be used as a protective coating on wood. Another object is to provide organic polyhydroxy silicate compounds and polymers that will chemically react with epoxy compounds to produce useful resins.

DESCRIPTION OF PREFERRED EMBODIMENTS

My invention will be illustrated in greater detail by the specific examples that follow, it being understood that these preferred embodiments are illustrative of, but not limited to, procedures which may be used in the production of organic polyhydroxy silicate compounds and polymers. Parts and percentages are by weight unless otherwise indicated.

EXAMPLE 1

About 150 parts by weight of sodium metasilicate pentahydrate are slowly added to about 75 parts by weight of concentrated sulfuric acid while agitating and keeping the temperature below 100° C. The reaction takes place under ambient pressure; oxygen is evolved and the reaction is complete in 1 to 2 hours, thereby producing a white granular silicic acid compound and sodium sulfate. The mixture is washed with water and filtered to remove the salt and water, thereby recovering the silicic acid compound. The silicic acid compound is air dried at 25° to 75° C.

About equal parts by weight of said silicic acid compound and glycerol and about 5% by weight of sodium carbonate, percentage based on the weight of the silicic acid and glycerol, are mixed. The mixture is then heated to just below the boiling point of glycerol for 20 to 30 minutes while agitating at ambient pressure, thereby producing light brown granules of glycerol silicate.

On further heating of the glycerol silicate at a temperature just below the boiling point of glycerol for 10 to 30 minutes, the glycerol silicate granules soften, then form a brown poly (glycerol silicate) polymer.

The poly (glycerol silicate) polymer is soluble in glycerol, water, propylene glycol, acetic acid, dilute sulfuric acid, dilute solution of alkali metal hydroxides and other organic solvents.

The glycerol silicate may be used as a filler in acrylic resin paints. The glycerol silicate will chemically react with dicarboxylic acids and anhydrides by the use of heat to produce resins. As an example, about one part by weight of glycerol silicate and about one part by weight of phthalic anhydride are mixed, then heated to above the melting temperature of phthalic anhydride for 30 to 90 minutes, thereby producing a light brown, hard, solid poly (phthalic glycerol silicate) resin. The resin is soluble in acetic acid, and when a solution of said resin in painted on wood, it forms a tough, protective coating.

The said poly (glycerol silicate) polymer, when mixed with toluene diisocyanate in equal weights and heated to about 90° C for 30 to 90 minutes, produces a rigid foam. The said foam is soluble in acetic acid and a solution of said foam, when painted on wood, forms a tough, clear, light brown, protective coating.

The poly (glycerol silicate) polymer is added to glacial acetic acid to form a solution and then filtered; about 15% to 25% of the silicic acid is filtered out. About half of the silicic acid that is filtered out has reacted with glycerol to form glycerol disilicate.

EXAMPLE II

About 20 parts by weight of sodium metasilicate are added to about 100 parts by weight of water, then stirred until the sodium metasilicate goes into solution. A dilute solution of sulfuric acid is added to the said solution until the pH is 5 to 7. The silicic acid precipitates as a gel. The water and sodium sulfate are filtered off; the gel is rewashed with water and filtered. The moist silicic acid gel and 3 parts by weight of sodium carbonate are added to 10 parts by weight of glycerol, mixed, then heated to just below the boiling point of glycerol for 20 to 60 minutes while agitating, thereby producing light brown granules of glycerol silicate. On further heating, at a temperature just below the boiling point of glycerol (200° to 280° C) for 10 to 30 minutes, the light brown granules soften, then produce a brown poly (glycerol silicate) polymer. The said polymer is soluble in acetic acid, and on filtering the solution, about 20 to 30% of the silicic acid is filtered out. About half of the silicic acid that is filtered out has reacted with the glycerol to produce a glycerol disilicate compound.

EXAMPLE III

About 50 parts by weight of silicic acid as produced in Example I, 75 parts by weight of glycerol and about 2 parts by weight of potassium carbonate are mixed, then heated to 200° to 290° C for 20 to 60 minutes while agitating at ambient pressure, thereby producing light brown granules of glycerol silicate.

EXAMPLE IV

About 50 parts by weight of silicic acid as produced in Example I, about 30 parts by weight of ethylene glycol and about 5 parts by weight of sodium carbonate are mixed, then heated to about the boiling point of ethylene glycol (150° to 190° C) while agitating at ambient pressure for 30 to 90 minutes, thereby producing a light brown granular mixture of ethylene glycol silicate and poly (ethylene glycol silicate) polymer.

The mixture of ethylene glycol silicate and poly (ethylene glycol silicate) polymer is soluble in glacial acetic acid. About 15% to 25% of the silicic acid and ethylene glycol disilicate are not soluble in acetic acid.

EXAMPLE V

About 50 parts by weight of silicic acid as produced in Example I, 75 parts by weight of diethylene glycol and 6 parts by weight of sodium carbonate are mixed, then heated to about the boiling point of diethylene glycol while agitating for 20 to 90 minutes, thereby producing a thick, light brown liquid, diethylene glycol silicate. On further heating at the above temperature for 20 to 30 minutes, a soft, solid, light brown poly (diethylene glycol silicate) polymer is produced.

The said polymer is soluble in ethylene glycol, dilute sulfuric acid, dilute sodium hydroxide solution, acetic acid and other organic and inorganic solvents. On filtering a solution of poly (diethylene glycol silicate) polymer, about 15 to 25% of the silicic acid is filtered out as silicic acid and diethylene glycol disilicate.

The said diethylene glycol silicate and poly (diethylene glycol silicate) polymer will chemically react with diiscocyanates, dicarboxyl acids and dicarboxyl anhydrides to form hard resins which are soluble in organic solvents such as acetic acid. A solution of these hard resins may be painted on wood and forms a tough, clear, light brown, protective coating.

EXAMPLE VI 50 parts by weight of silicic acid as produced in Example I, 100 parts by weight of triethylene glycol and 5 parts by weight of sodium carbonate are mixed then heated to a temperature near the boiling point of triethylene glycol (150° to 250° C) while agitating at ambient pressure for 20 to 90 minutes, thereby producing a light brown, liquid mixture of triethylene glycol silicate and poly (triethylene glycol silicate) polymer.

On filtration of the said light brown, liquid mixture, about 15% to 20% of the silicic acid is filtered out. Part of the silicic acid filtered out has reacted chemically with the triethylene glycol to produce triethylene glycol disilicate.

About an equal weight of the mixture of triethylene glycol silicate and poly (triethylene glycol silicate) polymer and an equal weight of toluene diisocyanate are mixed; then about 3% weight of water is added, and a foam is produced. The foam is heated to about 90° C for 30 to 90 minutes. The semi rigid foam is soluble in acetic acid, and when a solution of said foam is painted on wood, it forms a tough, clear, light, brown protective coating.

EXAMPLE VII 50 parts by weight of silicic acid as produced in Example I, about 100 parts by weight of polyethylene glycol (380 to 420 mol wt.) and 8 parts by weight of sodium carbonate are mixed, then heated to 180° to 250° C for 20 to 90 minutes while agitating at ambient pressure, thereby producing polyethylene glycol silicate.

EXAMPLE VIII

About 50 parts by weight of silicic acid as produced in Example I, about 50 parts by weight of propylene glycol and 1 part by weight of sodium carbonate are mixed then heated to 150° to 180° C while agitating for 30 to 90 minutes, thereby producing a light brown, granular mixture of propylene glycol silicate and poly (propylene glycol silicate) polymer.

EXAMPLE IX

About equal parts by weight of a dry potassium metasilicate, containing less than 6 mols of water per mol of potassium metasilicate, and potassium hydrogen sulfate are mixed. The mixture is agitated at ambient pressure, and the chemical reaction causes oxygen to evolve in 1 to 3 minutes; considerable heat is produced, and the chemical reaction is complete in 1 to 2 hours, thereby producing white granules of a silicic acid compound and potassium sulfate. The mixture is washed with water and filtered to remove the salt. The silicic acid compound is air dried at 25° to 75° C.

About 75 parts by weight of 1,4-butanediol, 50 parts by weight of said silicic acid and 3 parts by weight of potassium carbonate are mixed then heated to just below the boiling temperature of 1,4-butanediol for 20 to 60 minutes, thereby producing a light brown granular mixture of 1,4-butanediol silicate and poly (1,4-butanediol silicate) polymer.

EXAMPLE X 50 parts by weight of silicic acid as produced in Example IX, 75 parts by weight of 2,2'-oxydiethanol and 3 parts by weight of sodium silicate are mixed then heated to just below the boiling temperature of 2,2'-oxydiethanol while agitating for 20 to 60 minutes, thereby producing a thick, light brown liquid mixture of 2,2'-oxydiethanol silicate and poly (2,2'-oxydiethanol silicate) polymer.

The said light brown liquid mixture will react chemically with diisocyanates to produce resins which are soluble in organic solvents and may be used as varnishes.

EXAMPLE XI 50 parts by weight of silicic acid as produced in Example 1, 30 parts by weight of glycerol and 3 parts by weight of potassium hydroxide are mixed then heated to a temperature just below the boiling temperature of glycerol for 20 to 90 minutes, thereby producing light brown granules of glycerol disilicate, glycerol silicate and poly(glycerol) silicate.

EXAMPLE XII 50 parts by weight of silicic acid as produced in Example I, 100 parts by weight of cator oil and 3 parts by weight of sodium hydroxide are mixed and heated to 90° to 200° C for 20 to 90 minutes while agitating at ambient pressure, thereby producing a thick, tan castor oil silicate liquid.

The thick, tan castor oil silicate liquid will react chemically with an equal weight of toluene diisocyanate to produce a tough, semi-rigid urethane silicate form. The said castor oil silicate, toluene diisocyanate and 3% water are mixed, then heated to about 90° C for 30 to 90 minutes, thereby producing urethane silicate foam.

EXAMPLE XIII

About 50 parts by weight of silicic acid as produced in Example I, about 100 parts by weight of granular cane sugar and 10 parts by weight of sodium carbonate are mixed then heated to 90° to 200° C for 20 to 90 minutes, thereby producing a brown, solid cane sugar silicate. The cane sugar silicate is soluble in water, and on filtration of the solution, about 10 to 20% of the silicic acid is filtered out. About one half of the silicic acid that was filtered out had reacted chemically with the cane sugar.

EXAMPLE XIV

About 50 parts by weight of silicic acid as produced in Example I, about 150 parts by weight of a 35% aqueous solution of 2-butyne-1,4-diol and 5 parts by weight of sodium carbonate are mixed then heated to 80° to 120° C while agitating for 20 to 90 minutes, thereby producing a light brown mixture of 2-butyne-1,4-diol silicate and poly(2-butyne-1,4-diol) polymer.

EXAMPLE XV

About 50 parts by weight of silicic acid as produced in Example I, 100 parts by weight of linseed oil and 6 parts by weight of sodium carbonate are mixed then heated to 90° to 200° C for 20 to 90 minutes while agitating, thereby producing a thick, light brown, linseed oil silicate liquid.

The said linseed oil silicate may be used to modify the glyptal resins and react chemically with toluene diisocyanate to produce resins and foams.

EXAMPLE XVI

About 50 parts by weight of silicic acid as produced in Example I, 100 parts by weight of corn starch and 2 parts by weight of sodium carbonate are mixed, then heated to the softening temperature of the corn starch while agitating for 20 to 60 minutes thereby producing a dark brown starch silicate. About 75% of the starch silicate is soluble in water and the remaining portion are dark brown granules of starch silicate.

The starch silicate compound will react chemically with epoxy compounds, such as epichlorohydrin to produce useful resins.

Although specific material and conditions were set forth in the above Examples, these were merely illustrative of preferred embodiments of my invention. Various other compositions, such as the typical materials listed above may be used, where suitable. The reactive mixtures and products of my invention may have other agents added thereto to enhance or otherwise modify the reaction and products.

Other modifications of my invention will occur to those skilled in the art upon reading my disclosure. These are intended to be included within the scope of my invention, as defined in the appended claims.

I claim

1. The process for the production of organic hydroxy silicate compounds and their condensation products by the following steps:

(a) adding about 100 parts by weight of dry granular alkali metal metasilicate slowly to 50 parts by weight of concentrated sulfuric acid;

(b) agitating said mixture to keep the temperature below 100° C and oxygen evolves from the mixture, thereby (c) producing a white granular mixture of a silicic acid compound and alkali metal sulfate;

(d) washing said mixture with water, then filtering the mixture to remove the alkali metal sulfate and then air drying at 25° to 75° C, leaving a fine white granular silicic acid compound;

(e) mixing about 50 parts by weight of said silicic acid compound with about 30 to 100 parts by weight of a polyhydroxy alcohol compound;

(f) adding an alkali catalyst in the ratio of 1% to 10% by weight of the silicic acid compound and polyhydroxy alcohol compound;

(g) heating the said mixture to just below the boiling point of the polyhydroxy alcohol while agitating for about 20 to 90 minutes, thereby (h) producing a brown mixture of an organic hydroxy silicate compound and a poly (organic hydroxy silicate) polymer.

2. The process according to claim 1 wherein the dry alkali metasilicate is selected from the group consisting of sodium metasilicate and potassium metasilicate.

3. The process according to claim 1 wherein the polyhydroxy alcohol compound is selected from the group consisting of glycerol, ethylene glycol, propylene glycol, butylene glycol, trimethylene glycol, tetramethylene glycol, pentamethylene glycol, hexamethylene glycol, diethylene glycol, triethylene glycol, dipropylene glycol, tetraethylene glycol, polyethylene glycol, bis (B-hydroxyethyl) terephthlate, trimethol propane, trimethol ethane, 2,2'-oxyethanol, and 2-butyne-1,4-doil in an aqueous solution.

4. The process according to claim 1 wherein the polyhydroxyl alcohol compound is a vegetable oil with free hydroxyl radicals such as castor oil.

5. The process according to claim 1 wherein the polyhydroxyl alcohol compound is a carbohydrate and is selected from the group consisting of cane sugar, glucose, mannose, fructose and starches.

* * * * *